United States Patent [19]

Thunberg et al.

[11] Patent Number: 5,110,965

[45] Date of Patent: May 5, 1992

[54] PROCESS FOR THE PREPARATION OF SALTS OF IRON AMINO AND HYDROXY CARBOXYLIC ACID COMPLEXES

[75] Inventors: Jon C. Thunberg, Milford; Steven P. VanKouwenberg, Raymond, both of N.H.; Walter B. Begonis, Reading, Mass.

[73] Assignee: W.R. Grace & Co.-Conn., New York, N.Y.

[21] Appl. No.: 568,001

[22] Filed: Aug. 16, 1990

[51] Int. Cl.$^5$ .............................................. C07F 15/02
[52] U.S. Cl. ................................................... 556/148
[58] Field of Search ................ 556/138, 146, 147, 148

[56] References Cited

U.S. PATENT DOCUMENTS

| | | | |
|---|---|---|---|
| 3,115,511 | 12/1963 | Singer et al. | 556/148 |
| 3,767,689 | 10/1973 | Donovan et al. | 260/439 R |
| 3,867,419 | 2/1975 | Iwano et al. | 260/439 R |
| 4,216,144 | 8/1980 | Ashmead | 556/148 X |
| 4,364,871 | 12/1982 | Svatek et al. | 260/439 R |
| 4,438,040 | 3/1984 | Svatek et al. | 260/439 R |
| 4,558,145 | 12/1985 | Smith et al. | 556/148 |
| 4,830,716 | 5/1989 | Ashmead | 556/148 X |

FOREIGN PATENT DOCUMENTS

| | | |
|---|---|---|
| 3622364 | 1/1987 | Fed. Rep. of Germany . |
| 53-35929 | 7/1978 | Japan . |
| 58-21690 | 7/1981 | Japan . |
| 59-1675959 | 7/1984 | Japan . |
| 85562 | 2/1985 | Romania . |
| 802267 | 7/1978 | U.S.S.R. . |

*Primary Examiner*—Arthur C. Prescott
*Attorney, Agent, or Firm*—Kevin S. Lemack; William L. Baker

[57] ABSTRACT

A process of preparing iron chelates of amino and hydroxy carboxylic acids, comprising reacting an oxide of iron with an amino or hydroxy carboxylic acid and a base in the presence of ferrous ion or metallic iron as a catalyst. Additional base is added to the resulting chelant and oxidation may be carried out to convert any ferrous ion to ferric.

32 Claims, No Drawings

PROCESS FOR THE PREPARATION OF SALTS OF IRON AMINO AND HYDROXY CARBOXYLIC ACID COMPLEXES

BACKGROUND OF THE INVENTION

The present invention generally relates to salts of complexes of aminocarboxylic and hydroxycarboxylic acids, and in particular, to the process of preparing salts of iron complexes of aminocarboxylic and hydroxycarboxylic acids, such iron chelates have numerous applications, such as in agriculture, in photographic processing, and as food additives.

One conventional route to ferric ammonium EDTA complex is the reaction of diammonium EDTA solution with sponge iron at a temperature of 60° C. or higher for approximately 10 hours, thereby producing ferrous EDTA. The ferrous EDTA is then oxidized to ferric EDTA by air sparging or many hours. However, the production of the ferrous EDTA intermediate releases $H_2$, which is potentially explosive. The evolution of $H_2$ also often causes a foaming problem which limits the batch size. The sponge iron contains traces of sulfur and phosphorus; during the reaction with EDTA these are emitted as phosphine ($PH_3$) and hydrogen sulfide ($H_2S$) which generate obnoxious odors. In addition, the total processing time is in excess of 24 hours.

U.S. Pat. No. 4,558,145 to Smith et al discloses a process for preparing 5% iron solutions of the ferric chelate of hydroxyethlyenediaminetriacetic acid from the trisodium salt of that acid, nitric acid and metallic iron. The ferrous chelate thus produced is then converted to the ferric chelate by air oxidation.

Japanese Kokai 53-35929 discloses a process for preparing ferric chelates wherein a mixture of 5-74 weight % $Fe_3O_4$, 25-95 weight % iron, and depending on the circumstances, 0-60 weight % of a water soluble iron salt are made to react with a chelating agent or its alkaline salts in an aqueous medium not above room temperature. The ferrous chelate is simultaneously or subsequently oxidized to ferric by air sparging. This process has the advantage that little hydrogen is evolved; however, all the iron complex produced from the $Fe_3O_4$/Fe° reaction is ferrous iron and thus all must be oxidized to ferric iron.

Japanese Kokai 59-167595 discloses a process for Preparing ferric chelates wherein the rate of reaction of the chelating agent with hydrated iron oxide is accelerated by the addition of a reducing agent such as hydrazine or sodium hydrosulfite.

U.S. Pat. No. 3,767,689 to Donovan et. al. discloses a process for preparing water-soluble ammonium salts of ferric aminocarboxylic acid complexes by heating iron oxide with an aminocarboxylic acid or a partially neutralized aminocarboxylic acid in an aqueous medium, and neutralizing the resulting ferric complex by reacting it with a base, such as ammonium, sodium, or potassium hydroxide.

U.S. Pat. No. 4,364,871 to Svatek et. al. discloses a process for preparing aminopolycarboxylic acid chelates of iron by reacting ammonia and the aminopolycarboxylic acid in a mole ratio of about 1-1.5:1 ($NH_3$ aminopolycarboxylic acid) in the presence of iron oxide. After the iron oxide is completely reacted with the chelant, the mixture is cooled and sufficient ammonia is introduced to dissolve and maintain the iron chelate in solution. The reaction mixture is cooled, and contacted with air to oxidize any remaining ferrous to ferric.

These processes suffer from various drawbacks, such as the necessity of elevated reaction temperatures which results in the deleterious decomposition of the aminopolycarboxylic acid, the necessity to use expensive synthetic iron oxides and/or reducing agents to achieve acceptable reaction temperatures and times, the generation of all iron in the Fe(II) oxidation state, or the evolution of explosive hydrogen.

SUMMARY OF THE INVENTION

The problems of the prior art have been overcome by the present invention, which provides a process for preparing salts of iron complexes of aminocarboxylic and hydroxycarboxylic acids. Generally, the present invention involves reaction of the free acid, or the ammonium, sodium, lithium, or potassium salts or partial salts of an aminocarboxylic or hydroxycarboxylic acid, with an oxide of iron such as magnetite ($Fe_3O_4$) or hydrated iron oxide [Fe(OH)0] in the presence of a catalyst, followed by the addition of more base and, optionally, oxidation to convert any Fe(II) to Fe(III). The reaction proceeds at lower temperatures and more rapidly than prior art processes, thereby minimizing product decomposition and reaction time. No phosphine or hydrogen sulfide is emitted. In addition, no hydrogen gas is produced; therefore, no reduction of Fe(III) to Fe(II) occurs from hydrogen gas. Prior art processes which employ magnetite as the primary iron source generally require the use of expensive synthetic magnetite. In contrast, for some ligands, such as EDTA, the instant process can be practiced with inexpensive magnetite from natural sources.

In a preferred embodiment of the present invention, the reaction of magnetite and the salt or partial salt of an aminocarboxylic acid (such as $EDTAH_{3.5}(NH_4)_{0.5}$) or a hydroxycarboxylic acid (such as citric acid monoammonium salt) is catalyzed by the addition of a soluble ferrous salt, followed by addition of more base ($NH_3$ in the above instance) and then air oxidation.

In another embodiment of the present invention, the reaction of the iron oxide and the free acid or salt or partial salt of an aminocarboxylic or hydroxy carboxylic acid is catalyzed by the addition of trace amounts of finally divided metallic iron.

In a further embodiment of the present invention, the reaction of the iron oxide and the free acid or salt or partial salt of an aminocarboxylic or hydroxycarboxylic acid is catalyzed by the addition of trace amounts of the salt of the iron (II) complex being produced.

DETAILED DESCRIPTION OF THE INVENTION

Suitable aminocarboxylic acids that are useful in the present invention as the chelant moiety are those which are capable of chelating iron, including nitrilotriacetic acid (NTA); iminodiacetic acid (IDA); 1,2-propylenediaminetetraacetic acid (PDTA); 1,3-propanediaminetetraacetic acid (1,3-PDTA); ethylenediaminetetraacetic acid (EDTA); N-methyl, ethyl, propyl and butyl iminodiacetic acids; triethylenetriaminehexaacetic acid; ethyleneglycolbis(aminoethylether)tetraacetic acid; cyclohexane-1,2-diaminotetraacetic acid; diamino-2-propanoltetracetic acid; hydroxyethyliminodiacetic acid; dihydroxyethylglycine; ethanol diglycine; ethylenediamine ortho hydroxyphenylacetic acid; N-hydroxyethylethylenediaminetriacetic acid (HEDTA); and diethylenetriaminepentaacetic acid (DTPA). For IDA; N-methyl, ethyl, propyl and butyl iminodiacetic acids and for dihydroxyglycine and ethanol diglycine, the iron chelate will have a mole ratio of Fe:ligand of about 1:2. For purposes of simplicity, EDTA will be used hereinafter as illustrative of the aminocarboxylic acid, although it should be understood that other aminocarboxylic acids can be used.

Suitable hydroxy carboxylic acids that may be useful in the present invention as the chelant moiety are those which are capable of chelating iron, including citric acid, tartaric acid, lactic acid and gluconic acid.

Suitable iron oxides include magnetite and alpha and gamma hydrated iron oxides. The gamma hydrated iron oxide (lepidocrocite) is about twice as reactive as the alpha form (goethite). The iron in the hydrated oxides is in the $3^{30}$ oxidation state, therefore their use would generally eliminate the oxidation step. However, cost and availability (especially of the gamma form) may dictate that other oxides should be used. Hematite or red iron oxide is the least reactive iron oxide, and seems to result in excessive decomposition of the aminocarboxylic acid. Magnetite is the most reactive and the least expensive, and is therefore the preferred oxide. Synthetic magnetites are the purest form, but are relatively expensive. Some natural magnetites can be used where levels of impurities such as heavy metals, silica, and alumina, are acceptable. The presence of alumina and silica can cause severe filtration problems, rendering natural magnetites that are heavily contaminated with silica and alumina inappropriate. Some have surface properties which render them inert in the present process. The preferred natural magnetite is Tamms Magnetite, available from Tamms Industries. The preferred synthetic magnetite is Mapico Black. Of these, Tamms Magnetite is preferred due to its lower cost.

Where synthetic magnetites are used, the reaction temperature employed with EDTA should be about 40° C., preferably about 40–60° C., most preferably about 40–45° C.

Natural magnetites require higher reaction temperatures of at least about 60° C. with EDTA, preferably about 60° C.–80° C., most preferably about 60°–65° C.

Ligands other than EDTA may require higher reaction temperatures with both synthetic and natural magnetites, which one skilled in the art readily will be able to determine.

A mixture of magnetite and sponge iron (above catalytic amounts) also could be used, but it produces a slurry of only the ferrous chelate. Longer oxidation is then required to convert Fe(II) to Fe(III), which, in turn, would lead to greater decomposition of the product. The all-magnetite process produces a slurry in which only 20–25% of the total iron is in the ferrous state; the balance is already ferric. As a result, less time is required for air oxidation and decomposition of product is mitigated.

The selection of a suitable base depends upon the particular complex salt that is desired. Ferric ammonium EDTA is prepared by employing $NH_3$ (such as 28% $NH_3$) in a mole ratio of $NH_3$: $EDTAH_4$ of no greater than about 2.0:1.0, preferably about 0.1–1.0:1.0, most preferably about 0.5:1.0. Similarly, ferric sodium EDTA and ferric potassium EDTA can be prepared using NaOH and KOH respectively, as the base, in similar amounts. Where the starting acid is in the form of its salt or partial salt, the neutralizing base is one whose cation is also the salifying ion.

The rates of reaction of the oxide with the acid are pH and temperature dependent. In the absence of a catalyst, reaction temperatures of about 90°–110° C. are necessary. In the process of the present invention, rates of reaction can be increased in the order of about 2–10 fold by the use of a trace amount of a soluble (.e(II) salt, a trace amount of Fe°, or, a trace amount of the salt of the iron (II) complex being produced, to catalyze the reaction of the oxide with the acid. As the Fe(II) salt, any ferrous salt which will dissolve in the reaction mixture and whose anion is not deleterious to the process or end application of the product can be used. The preferred inorganic salt is $FeSO_4.xH_2O$ because it is inexpensive, very soluble in the reaction mixture, and sulfate causes no problems in the end application. Other suitable inorganic salts include ferrous carbonate, chloride, bromide and nitrate. The preferred organic salt is the ferrous chelate of the ligand being produced. Other suitable organic salts include ferrous gluconate, citrate and glycolate. The salt should be used in a trace amount, which for $FeSO_4.xH_2O$ (and EDTA as the ligand) is a contained iron mole ratio of $FeSO_4.xH_2O$:$Fe_3O_4$ of about 0.002–0.05:1, preferably about 0.01–0.02:1, an equivalent amount for the other salts and about 0.0007–0.017:1 for Fe°.

In the preparation of ferric ammonium EDTA, for example, after the catalyzed reaction of the iron oxide with $EDTAH_{3.5}(NH_4)_{0.5}$, additional base ($NH_3$) is added. The mono ammonium salt, $EDTANH_4Fe$, can be produced by limiting the total $NH_3$ charge to 1.0 moles $NH_3$: 1.0 moles $EDTAH_4$ Ferric ammonium EDTA complex, $EDTA(NH_4)_2FeOH$ is formed where the total charge of $NH_3$ is higher. A suitable amount of $NH_3$ added after the catalyzed reaction is about 1.4–2.0 moles per mole of $EDTAH_4$.

Oxidation of any Fe(II) to Fe(III) can be accomplished by any suitable means, such as by sparging with air or oxygen. Air oxidation is preferred. At an oxidation temperature above about 40° C., decomposition of the amino or hydroxy carboxylic acid moiety increases rapidly. Preferably, oxidation is carried out in a temperature range of about 25°–35° C.

The preferred order of addition of reactants is as follows. Water, the iron oxide, and base are mixed prior to the addition of the acid. (If the base is added after mixing water, the acid and the iron oxide, the subsequent reaction may become sluggish and the reaction incomplete, especially with natural magnetites). When the temperature is equilibrated, the catalyst is then added. Thus, in the Preferred process of preparing EDTA($NH_4$)Fe, water, ammonia, and synthetic magnetite are mixed, EDTA acid is added and the resulting slurry is equilibrated at about 40° C. Ferrous sulfate catalyst is then added, so that the mole ratios (Fe compounds in terms of contained Fe) of $NH_3$:EDTA:magnetite:$FeSO_4$ are about 0.530:1.06:1.00:0.01. After the chelation reaction is complete, approximately 25% of the total iron is as Fe(II) and approximately 75% is as Fe(III). The slurry is neutralized with $NH_3$ to a PH of about 5–7 and is air-oxidized at a temperature of about 30° C. The Fe(III) NH EDTA solution is then converted to the complex (EDTA(NH 2FeOH) by the addition of more $NH_3$, diluted to final concentration, and filtered to remove any small amount of insoluble residue derived from the magnetite. To produce solid products, crystallization or a total drying process such as spray drying can be used to produce the mono ammonium, sodium or potassium salt of the Fe(III) chelate.

The present invention will now be illustrated by the following non-limiting examples.

EXAMPLE 1

In order to demonstrate the catalytic effect of the addition of ferrous ion, a series of runs was made using $NH_3$ EDTA mole ratios of 0.5 and 1.0:1.0 at 40° C. and 60° C. The mole ratio of EDTA:TOTAL Fe was 1.10:1.0. The mole ratio of Fe(II):Fe in magnetite was 0.01:1.0. The magnetite used was Mapico Black. In runs 1, 7 and 8, the pH was raised to approximately 6 with $NH_3$ prior to air sparging. The runs summarized in Table I.

At the $NH_3$: $EDTAH_4$ mole ratio of 0.5:1.0 and at 40° C., the time required for complete dissolution of the magnetite was approximately 45 minutes Run no. 4 demonstrates the catalytic effect of Fe(II). In that run, the $EDTAH_4/NH_3$ mixture was equilibrated at 40° C. and held at that temperature for 3 hours, and no reaction occurred. Upon adding $FeSO_4$, the reaction began immediately. Run no. 3 shows that the reaction proceeds without the need for Fe(II) catalyst if the temperature is raised to 60° C.

At the $NH_3$: $EDTAH_4$ mole ratio of 1.0:1.0, the reaction is much slower than at the lower ratio. In Run no. 5, the $NH_3/EDTAH_4$/magnetite mixture stirred at 40° C. with Fe(II) catalyst present, and no reaction occurred until the temperature was raised to 60° C. Similarly, in run no. 6, the mixture without catalyst stirred at 60° C. for 30 minutes with no reaction occurring, and, upon addition of Fe(II), the reaction started immediately.

EXAMPLE 2

A survey of the relative reaction rates of various ligands with magnetite as a function of mole ratio of base:ligand (or pH) was run. Water, ligand in the free acid form, ammonia solution, and synthetic magnetite were weighed into 20 ml pressure tubes. The pH was measured, then ferrous sulfate was weighed into some of the tubes and the tubes were sealed with a threaded teflon stopper fitted with an O-ring seal. The tubes were mounted on a rotating rack inside of a forced draft oven. The oven was turned on and the rack was rotated. When the oven temperature reached 70° C. a timer was started. The tubes were periodically examined. By bringing the tubes between the poles of a heavy horseshoe magnet, it was possible to determine when the magnetite had dissolved.

These experiments are summarized in Table II. These data show that the ferrous catalyzed magnetite/ligand reaction is generally applicable to a wide variety of ligands, but that the optimum conditions are specific for each, and the rates of reaction vary widely. The generally operable pH range is about 2.2–4.2. There may be other ligands which may have optimum pH ranges somewhat outside of this range; those skilled in the art readily will be able to determine the optimum conditions for ligands other than those included in Table II.

EXAMPLE 3

The general procedure of Example 2 was used but the ligand was Hamp-ol ®-120, a commercial 41.3% solution of hydroxyethylenediaminetriacetic acid (HEDTA) trisodium salt. The ligand was weighed into a series of tubes.

TABLE 1

| Run No. | Mole Ratio NH3:1.00 EDTAH4 | Reation Temp. °C. | Time to Dissolve All Fe (Min) | Air Sparge Temp., °C. | Minutes | Comments For those lots which were air sparged. the pH was raised $10^{-6}$ with NH3 before sparging began. |
|---|---|---|---|---|---|---|
| 1 | 0.5 | 40 | 45 | 40 | 90 | |
| 2 | 0.5 | 40 | 45 | | 0 | |
| 3 | 0.5 | 60 | ~30 | | 0 | No Fe(II) added |
| 4 | 0.5 | 40 | 45–60 | | 0 | Held 3 hr @ 40° C. before Fe(II) added - no reaction until Fe(II) was added |
| 5 | 1.0 | 40/60 | | | 0 | No reaction after 60 min with Fe(II) present - heated to 60° C. - reaction began immediately |
| 6 | 1.0 | 60 | 60 | | | Held 30 min @ 60° C. before Fe(II) added - no reaction until Fe(II) added |
| 7* | 1.0 | 60 | 60 | 30 | 90 | Repeat of No. 6 but Fe(II) added as soon as T reached 60° C. - reacted immediately. This lot was air sparged. |
| 8* | 0.5 | 40 | 90 | 30 | 90 | |

| | Analytical Data | | | | | |
|---|---|---|---|---|---|---|
| | Ferrous Iron | | Ferric Iron | | Free EDTA | |
| No. | 1st | Final | 1st | Final | 1st | Final |
| 1 | 1.48% | 0.11% | 5.89% | 5.56% | n.a. | n.a. |
| 2 | 1.73% | n.a. | 5.89% | n.a. | n.a. | n.a. |
| 3 | 1.58% | n.a. | 5.76% | n.a. | n.a. | n.a. |
| 4 | 2.07% | | 5.35% | | | |
| 5 | | | | | | 3.48% |
| 6 | | | | | | 4.17% |
| 7* | 2.09% | 0.22% | 7.11% | 7.48% | 4.54% | n.a. |
| 8* | 1.75% | 0.28% | 6.98% | 6.95% | 6.12% | n.a. |

*Water charge reduced to give 7% total Fe
Note: 1st = sample at end of dissolution or just before sparge

TABLE II

| | SUMMARY OF LIGAND/MAGNETITE SCREENING PROGRAM | | | | | | | | |
|---|---|---|---|---|---|---|---|---|---|
| | | EDTA | | | | | | | |
| | LIGAND | A | E* | B | F* ** | C | G* | D | H* |
| MOLE RATIO | NH3:Ligand | 0.00 | 0.00 | 0.50 | 0.50 | 1.00 | 1.00 | 1.50 | 1.50 |
| | Ligand:Fe in magnetite | 1.10 | 1.12 | 1.10 | 1.12 | 1.10 | 1.12 | 1.10 | 1.12 |

TABLE II-continued

SUMMARY OF LIGAND/MAGNETITE SCREENING PROGRAM

|  |  |  |  |  |  |  |  |  |  |
|---|---|---|---|---|---|---|---|---|---|
|  | Fe in magnetite | 1.00 | 1.00 | 1.00 | 1.00 | 1.00 | 1.00 | 1.00 | 1.00 |
|  | FeSO4:Fe in magnetite | 0.000 | 0.020 | 0.000 | 0.020 | 0.000 | 0.020 | 0.000 | 0.020 |
| MILLI-MOLES | Ligand | 19.25 | 19.25 | 19.25 | 19.65 | 19.25 | 19.64 | 19.25 | 19.64 |
|  | NH3 | 0.00 | 0.00 | 9.63 | 9.82 | 19.25 | 19.64 | 28.88 | 29.45 |
|  | Fe in magnetite | 17.50 | 17.50 | 17.50 | 17.50 | 17.50 | 17.50 | 17.50 | 17.50 |
|  | FeSO4 | 0 | 0.35 | 0 | 0.35 | 0 | 0.35 | 0 | 0.35 |
| TOTAL GRAMS |  | 15.00 | 15.00 | 15.00 | 15.00 | 15.00 | 15.00 | 15.00 | 15.00 |
| pH | initial | 3.10 | 3.13 | 4.19 | 4.18 | 4.41 | 4.38 | 4.56 | 4.55 |
|  | final | 0.73 | 0.78 | 2.32 | 2.40 | 2.97 | 2.98 | 5.77 | 5.77 |
| MINUTES TO DISSOLVE |  | ~80 | ~60 | ~80 | >5 <10 | ~80 | ~20 | >180 | >180 |

DTPA

|  | LIGAND | A | B | F* ** | C | G* | D | H* | E | I* |
|---|---|---|---|---|---|---|---|---|---|---|
| MOLE RATIO | NH3:Ligand | 0.00 | 0.50 | 0.50 | 1.00 | 1.00 | 1.50 | 1.50 | 2.00 | 2.00 |
|  | Ligand:Fe in magnetite | 1.10 | 1.10 | 1.12 | 1.10 | 1.12 | 1.10 | 1.12 | 1.10 | 1.12 |
|  | Fe in magnetite | 1.00 | 1.00 | 1.00 | 1.00 | 1.00 | 1.00 | 1.00 | 1.00 | 1.00 |
|  | FeSO4:Fe in magnetite | 0.000 | 0.000 | 0.020 | 0.000 | 0.020 | 0.000 | 0.020 | 0.000 | 0.020 |
| MILLI-MOLES | Ligand | 19.25 | 19.25 | 19.64 | 19.25 | 19.64 | 19.25 | 19.64 | 19.25 | 19.64 |
|  | NH3 | 0.00 | 9.63 | 9.82 | 19.25 | 19.64 | 28.88 | 29.45 | 38.50 | 39.27 |
|  | Fe in magnetite | 17.50 | 17.50 | 17.50 | 17.50 | 17.50 | 17.50 | 17.50 | 17.50 | 17.50 |
|  | FeSO4 | 0 | 0 | 0.35 | 0 | 0.35 | 0 | 0.35 | 0 | 0.35 |
| TOTAL GRAMS |  | 15.00 | 15.00 | 15.00 | 15.00 | 15.00 | 15.00 | 15.00 | 15.00 | 15.00 |
| pH | initial | 2.38 | 3.55 | 3.60 | 3.83 | 3.87 | 4.05 | 4.08 | 4.31 | 4.37 |
|  | final | 2.12 | 2.16 | 2.05 | 2.68 | 2.67 | 3.58 | 3.56 | 4.62 | 4.70 |
| MINUTES TO DISSOLVE |  | 30 | 90 | 5 to 10 | ~135 | 15 | 180 | 30 | 330 | ~90 |

HEDTA

|  | LIGAND | A | E* ** | B | F* ** | C | G* | D | H* |
|---|---|---|---|---|---|---|---|---|---|
| MOLE RATIO | NH3:Ligand | 0.00 | 0.00 | 0.25 | 0.25 | 0.50 | 0.50 | 1.00 | 1.00 |
|  | Ligand:Fe in magnetite | 1.10 | 1.12 | 1.10 | 1.12 | 1.10 | 1.12 | 1.10 | 1.12 |
|  | Fe in magnetite | 1.00 | 1.00 | 1.00 | 1.00 | 1.00 | 1.00 | 1.00 | 1.00 |
|  | FeSO4:Fe in magnetite | 0.000 | 0.020 | 0.000 | 0.020 | 0.000 | 0.020 | 0.000 | 0.020 |
| MILLI-MOLES | Ligand | 19.25 | 19.64 | 19.25 | 19.64 | 19.25 | 19.64 | 19.25 | 19.64 |
|  | NH3 | 0.00 | 0.00 | 4.81 | 4.91 | 9.63 | 9.82 | 19.25 | 19.64 |
|  | Fe in magnetite | 17.50 | 17.50 | 17.50 | 17.50 | 17.50 | 17.50 | 17.50 | 17.50 |
|  | FeSO4 | 0 | 0.35 | 0 | 0.35 | 0 | 0.35 | 0 | 0.35 |
| TOTAL GRAMS |  | 15.00 | 15.00 | 15.00 | 15.00 | 15.00 | 15.00 | 15.00 | 15.00 |
| pH | initial | 2.20 | 2.22 | 3.26 | 3.29 | 3.65 | 3.68 | 4.30 | 4.28 |
|  | final | 2.11 | 2.09 | 2.58 | 2.55 | 3.09 | 3.04 |  | 2.11 |
| MINUTES TO DISSOLVE |  | 50 | 15 | 80 | 15 | ~120 | 30 | >>240 | ~150 |

1,3-PDTA

|  | LIGAND | A | C* ** | B | D* |
|---|---|---|---|---|---|
| MOLE RATIO | NH3:Ligand | 0.50 | 0.50 | 1.00 | 1.00 |
|  | Ligand:Fe in magnetite | 1.10 | 1.12 | 1.10 | 1.12 |
|  | Fe in magnetite | 1.00 | 1.00 | 1.00 | 1.00 |
|  | FeSO4:Fe in magnetite | 0.000 | 0.020 | 0.000 | 0.020 |
| MILLI-MOLES | Ligand | 19.25 | 19.44 | 19.25 | 19.44 |
|  | NH3 | 9.63 | 9.72 | 19.25 | 19.44 |
|  | Fe in magnetite | 17.50 | 17.50 | 17.50 | 17.50 |
|  | FeSO4 | 0 | 0.35 | 0 | 0.35 |
| TOTAL GRAMS |  | 15.00 | 15.00 | 15.00 | 15.00 |
| pH | initial | 3.16 | 3.17 | 3.44 | 3.45 |
|  | final | 2.58 | 2.65 | 3.37 | 3.32 |
| MINUTES TO DISSOLVE |  | >>300 | ~150 | >300 | >120 <180 |

NTA

|  | LIGAND | A | E* ** | B | F* | C | G* | D | H* |
|---|---|---|---|---|---|---|---|---|---|
| MOLE RATIO | NH3:Ligand | 0.00 | 0.00 | 0.25 | 0.25 | 0.50 | 0.50 | 1.00 | 1.00 |
|  | Ligand:Fe in magnetite | 1.10 | 1.12 | 1.10 | 1.12 | 1.10 | 1.12 | 1.10 | 1.12 |
|  | Fe in magnetite | 1.00 | 1.00 | 1.00 | 1.00 | 1.00 | 1.00 | 1.00 | 1.00 |
|  | FeSO4:Fe in magnetite | 0.000 | 0.020 | 0.000 | 0.020 | 0.000 | 0.020 | 0.000 | 0.020 |
| MILLI-MOLES | Ligand | 19.25 | 19.64 | 19.25 | 19.64 | 19.25 | 19.64 | 19.25 | 19.64 |
|  | NH3 | 0.00 | 0.00 | 4.81 | 4.91 | 9.63 | 9.82 | 19.25 | 19.64 |
|  | Fe in magnetite | 17.50 | 17.50 | 17.50 | 17.50 | 17.50 | 17.50 | 17.50 | 17.50 |
|  | FeSO4 | 0 | 0.35 | 0 | 0.35 | 0 | 0.35 | 0 | 0.35 |
| TOTAL GRAMS |  | 15.00 | 15.00 | 15.00 | 15.00 | 15.00 | 15.00 | 15.00 | 15.00 |
| pH | initial | 2.34 | 2.38 | 3.17 | 3.15 | 3.30 | 3.29 | 3.49 | 3.47 |
|  | final |  | 2.51 |  | 2.74 | 4.26 | 4.09 | 4.52 | 4.60 |
| MINUTES TO DISSOLVE |  | >>180 | 60 to 75 | >>180 | ~120 | ~90 | ~90 | >150 | ~150 |

CITRIC ACID

|  | LIGAND | I | M* | J | N* | K | O* | L | P* ** |
|---|---|---|---|---|---|---|---|---|---|
| MOLE RATIO | NH3:Ligand |  | 0.00 | 0.00 | 0.25 | 0.25 | 0.50 | 0.50 | 1.00 | 1.00 |

TABLE II-continued

| | | | | | | | | | |
|---|---|---|---|---|---|---|---|---|---|
| | SUMMARY OF LIGAND/MAGNETITE SCREENING PROGRAM | | | | | | | | |
| | Ligand:Fe in magnetite | 1.10 | 1.12 | 1.10 | 1.12 | 1.10 | 1.12 | 1.10 | 1.12 |
| | Fe in magnetite | 1.00 | 1.00 | 1.00 | 1.00 | 1.00 | 1.00 | 1.00 | 1.00 |
| | FeSO4:Fe in magnetite | 0.000 | 0.020 | 0.000 | 0.020 | 0.000 | 0.020 | 0.000 | 0.020 |
| MILLI-MOLES | Ligand | 19.25 | 19.64 | 19.25 | 19.64 | 19.25 | 19.64 | 19.25 | 19.64 |
| | NH3 | 0.00 | 0.00 | 4.81 | 4.91 | 9.63 | 9.82 | 19.25 | 19.64 |
| | Fe in magnetite | 17.50 | 17.50 | 17.50 | 17.50 | 17.50 | 17.50 | 17.50 | 17.50 |
| | FeSO4 | 0 | 0.35 | 0 | 0.35 | 0 | 0.35 | 0 | 0.35 |
| TOTAL GRAMS | | 15.00 | 15.00 | 15.00 | 15.00 | 15.00 | 15.00 | 15.00 | 15.00 |
| pH | initial | 1.19 | 1.20 | 2.17 | 2.22 | 2.63 | 2.62 | 3.36 | 3.33 |
| | final | | | | | | | 3.60 | 3.23 |
| MINUTES TO DISSOLVE | | >>180 | >>180 | >>180 | >>180 | >>180 | >>180 | 60 | 15 to 50 |

Notes:
Iron compounds are expressed in terms of contained Fe
Magnetite is Mapico Black, a synthetic magnetite
Temperature is 70° C.
*designates mixtures containing ferrous sulfate
**designates most rapid reaction of the set Nitric acid was added to each to adjust each to various pH values. Synthetic magnetite was then added. Ferrous sulfate was added to selected tubes. The tubes were then rotated in the oven at 70° C. and observed for dissolution of the magnetite as in Example 2 The results are summarized in Table III.

The optimum pH (2.8) corresponded approximately to neutralization of the contained HEDTA to the free acid. Without the addition of ferrous sulfate, the time required to dissolve the magnetite was 60-105 minutes. With ferrous sulfate present, the time needed was 15-30 minutes at an HN03:ligand mole ratio of 3.07:1.

EXAMPLE 4

The general procedure of Example 2 was used. Optimum ammonia:ligand mole ratios for various ligands were used. Instead of ferrous sulfate, the catalyst was finely divided metallic iron, commonly known as sponge iron. The amount of sponge iron used was chemically equivalent to the amount of ferrous sulfate used in Example 2. The results are summarized in Table IV.

The results demonstrate that sponge iron is an effective catalyst.

EXAMPLE 5

To a 1 liter stirred vessel was added 315 g of water, 66.7 g of natural magnetite (0.850 moles of contained Fe), and 25.6 g of 29.4% NH3 (0.442 moles). To this mixture was added 258.4 g of EDTA acid (0.884 moles).

TABLE III

| | | SUMMARY OF [LIGAND(Na)x + HNO3] MAGNETITE SCREENING PROGRAM | | | | | | | |
|---|---|---|---|---|---|---|---|---|---|
| | | Hamp-Ol 120 + HNO3 | | | | | | | |
| | LIGAND | 48-C | 48-D* | 48-A | 48-B* | 50-E | 50-F* ** | 50-G | 50-H* |
| MOLE RATIO | HNO3:Ligand | 2.67 | 2.68 | 2.88 | 2.88 | 3.08 | 3.07 | 3.28 | 3.28 |
| | Ligand:Fe in magnetite | 1.10 | 1.12 | 1.10 | 1.12 | 1.10 | 1.12 | 1.10 | 1.12 |
| | Fe in magnetite | 1.00 | 1.00 | 1.00 | 1.00 | 1.00 | 1.00 | 1.00 | 1.00 |
| | FeSO4:Fe in magnetite | 0.000 | 0.020 | 0.000 | 0.020 | 0.000 | 0.020 | 0.000 | 0.020 |
| MILLI-MOLES | Ligand | 13.20 | 13.46 | 13.20 | 13.46 | 13.20 | 13.46 | 13.20 | 13.46 |
| | HNO3 | 35.27 | 36.03 | 38.00 | 38.76 | 40.62 | 41.38 | 43.24 | 44.11 |
| | Fe in magnetite | 12.00 | 12.00 | 12.00 | 12.00 | 12.00 | 12.00 | 12.00 | 12.00 |
| | FeSO4 | 0 | 0.24 | 0 | 0.24 | 0 | 0.24 | 0 | 0.24 |
| TOTAL GRAMS | | 15.19 | 15.55 | 15.44 | 15.80 | 15.68 | 16.04 | 15.92 | 16.29 |
| pH | initial | 3.79 | 3.80 | 3.32 | 3.28 | 2.87 | 2.84 | 2.54 | 2.52 |
| | final | | | | 3.78 | 3.22 | 3.10 | 2.81 | 2.75 |
| MINUTES TO DISSOLVE | | >>150 | >>150 | >>150 | >90 <120 | >90 <105 | >15 <30 | >60 <75 | >30 <45 |
| % Fe IN FINAL SOLUTION (calculated) | | | | | 4.33% | 4.27% | 4.26% | 4.21% | 4.20% |

Notes:
Iron compounds are expressed in terms of contained Fe
Magnetite is Mapico Black, a synthetic magnetite
Temperature is 70° C.
*designates mixtures containing ferrous sulfate
**designates most rapid reaction of the set

TABLE IV

| | SUMMARY OF LIGAND/IRON(0)/MAGNETITE SCREENING PROGRAM | | | | | | |
|---|---|---|---|---|---|---|---|
| | | EDTA | | DTPA | | HEDTA | |
| | LIGAND | 1 | 1A | 2 | 2A | 3 | 3A |
| | Fe(0) PRESENT | No | Yes | No | Yes | No | Yes |
| MOLE RATIO | NH3:Ligand | 0.50 | 0.50 | 0.50 | 0.50 | 0.00 | 0.00 |
| | Ligand:Fe in magnetite | 1.10 | 1.11 | 1.10 | 1.11 | 1.10 | 1.11 |
| | Fe in magnetite | 1.00 | 1.00 | 1.00 | 1.00 | 1.00 | 1.00 |
| | Fe(0):Fe in magnetite | 0.0000 | 0.0067 | 0.0000 | 0.0067 | 0.0000 | 0.0067 |

TABLE IV-continued
SUMMARY OF LIGAND/IRON(0)/MAGNETITE SCREENING PROGRAM

| | | | | | | | |
|---|---|---|---|---|---|---|---|
| MILLI-MOLES | Ligand | 19.25 | 19.38 | 19.25 | 19.38 | 19.25 | 19.38 |
| | NH3 | 9.63 | 9.69 | 9.63 | 9.69 | 0.00 | 0.00 |
| | Fe in magnetite | 17.50 | 17.50 | 17.50 | 17.50 | 17.50 | 17.50 |
| | Sponge Iron | 0.0000 | 0.1167 | 0.0000 | 0.1167 | 0.0000 | 0.1167 |
| TOTAL GRAMS | | 15.00 | 15.00 | 15.00 | 15.00 | 15.00 | 15.00 |
| pH | initial | 4.18 | 4.18 | 3.59 | 3.60 | 2.20 | 2.20 |
| | final | 2.36 | 2.37 | 2.98 | 3.01 | 2.08 | 2.11 |
| MINUTES TO DISSOLVE | | >60 <75 | <15 | >75 <90 | >15 <30 | >30 <45 | >15 <30 |

| | | 1,3-PDTA | | Citric Acid | | Hamp-Ol 120 + HNO3 | |
|---|---|---|---|---|---|---|---|
| | LIGAND | 4 | 4A | 6 | 6A | 7 | 7A |
| | Fe(0)PRESENT | No | Yes | No | Yes | No | Yes |
| MOLE RATIO | NH3:Ligand | 0.50 | 0.50 | 1.00 | 1.00 | 0.00 | 0.00 |
| | HNO3:Ligand | 0.00 | 0.00 | 0.00 | 0.00 | 3.08 | 3.08 |
| | Ligand:Fe in magnetite | 1.10 | 1.11 | 1.10 | 1.11 | 1.10 | 1.11 |
| | Fe in magnetite | 1.00 | 1.00 | 1.00 | 1.00 | 1.00 | 1.00 |
| | Fe(0):Fe in magnetite | 0.0000 | 0.0067 | 0.0000 | 0.0067 | 0.0000 | 0.0067 |
| MILLI-MOLES | Ligand | 19.25 | 19.38 | 19.25 | 19.38 | 13.20 | 13.29 |
| | NH3 | 9.63 | 9.69 | 19.25 | 19.38 | 0.00 | 0.00 |
| | HNO3 | 0.00 | 0.00 | 0.00 | 0.00 | 40.59 | 40.86 |
| | Fe in magnetite | 17.50 | 17.50 | 17.50 | 17.50 | 12.00 | 12.00 |
| | Sponge Iron | 0.0000 | 0.1167 | 0.0000 | 0.1167 | 0.0000 | 0.0800 |
| TOTAL GRAMS | | 15.00 | 15.00 | 15.00 | 15.00 | 15.68 | 15.78 |
| pH | initial | 3.21 | 3.22 | 3.40 | 3.40 | 2.81 | 2.81 |
| | final | | 2.68 | 3.54 | 3.54 | 3.24 | 3.30 |
| MINUTES TO DISSOLVE | | >>210 | ~210 | >75 <90 | >30 <45 | ~105 | >45 <60 |

ORDER OF LIGAND REACTION RATES: EDTA > DTPA = HEDTA > Citric Acid > Hamp-Ol 120/HNO3 > 1,3-PDTA
Notes:
Iron compounds are expressed in terms of contained Fe
Magnetite is Mapico Black, a synthetic magnetite
Temperature is 70° C.

The pH of the resulting mixture was 4.0. The slurry was heated to 63° C. and 2.36 g of $FeSO_4.7H_2O$ (0.009 moles) was added. The temperature was maintained at 60–65° C. After 90 minutes the magnetite had dissolved and the pH had dropped to 2.35 and was stable, thus indicating that the reaction was finished. A portion of this slurry was removed to be used as catalyst for the succeeding run. By analysis, the ferrous iron concentration of this sample was 1.77%.

The previous reaction was repeated except that 26.8 g (0.008 moles of Fe(II)) of the retained slurry from the first run was added instead of ferrous sulfate. The reaction was finished and the pH was stable within 60 minutes.

This example demonstrates that the ferrous chelate of the product being produced (in this case, ferrous ammonium EDTA) is an excellent catalyst for the system.

EXAMPLE 6

The general procedure of Example 2 was used but with gamma hydrated iron oxide instead of magnetite as the iron source. The optimum ammonia:ligand mole ratios previously found for the various ligands with magnetite were used. Tests were run at either 110° C. or 100° C. The results are summarized in Table V.

The data of Table V show that ferrous ion catalyzes the reaction of hydrated iron oxide with aminocarboxylic acids, but the rates of reaction are slower than with magnetite, and the reaction temperature is significantly higher than with magnetite.

TABLE V
SUMMARY OF LIGAND/GAMMA HYDRATED IRON OXIDE SCREENING PROGRAM

| | LIGAND | EDTA | | HEDTA | | NTA | |
|---|---|---|---|---|---|---|---|
| | EXPT. NO. | 13 | 13 | 13 | 13 | 11 | 11 |
| | TEMPERATURE, °C. | 100° C. | 100° C. | 100° C. | 100° C. | 110° C. | 110° C. |
| | FeSO4 PRESENT | No | Yes | No | Yes | No | Yes |
| MOLE RATIO | NH3:Ligand | 0.50 | 0.50 | 0.00 | 0.00 | 0.00 | 0.00 |
| | Ligand:Fe in iron oxide | 1.10 | 1.12 | 1.10 | 1.12 | 1.10 | 1.12 |
| | Fe in iron oxide | 1.00 | 1.00 | 1.00 | 1.00 | 1.00 | 1.00 |
| | FeSO4:Fe in iron oxide | 0 | 0.02 | 0 | 0.02 | 0 | 0.02 |
| MILLI-MOLES | Ligand | 19.25 | 19.64 | 19.25 | 19.64 | 19.25 | 19.64 |
| | NH3 | 9.63 | 9.82 | 0.00 | 0.00 | 0.00 | 0.00 |
| | Fe in iron oxide | 17.50 | 17.50 | 17.50 | 17.50 | 17.50 | 17.50 |
| | FeSO4 | 0 | 0.35 | 0 | 0.35 | 0 | 0.35 |
| TOTAL GRAMS | | 15.00 | 15.00 | 15.00 | 15.00 | 15.00 | 15.00 |
| pH | initial | 4.17 | 4.19 | 2.24 | 2.21 | 2.16 | 2.15 |
| | final | 1.93 | 1.64 | 2.46 | 2.36 | 2.31 | 1.84 |
| MINUTES TO DISSOLVE | | >120 <150 | >60 <90 | >120 <150 | >60 <90 | >>240 | >90 <120 |

| | LIGAND | 1,3-PDTA | | Citric Acid | |
|---|---|---|---|---|---|
| | EXPT. NO. | 11 | 11 | 11 | 11 |
| | TEMPERATURE, °C. | 110° C. | 110° C. | 110° C. | 110° C. |
| | FeSO4 PRESENT | No | Yes | No | Yes |
| MOLE RATIO | NH3:Ligand | 0.50 | 0.50 | 1.00 | 1.00 |
| | Ligand:Fe in iron oxide | 1.10 | 1.12 | 1.10 | 1.12 |
| | Fe in iron oxide | 1.00 | 1.00 | 1.00 | 1.00 |

TABLE V-continued

| | SUMMARY OF LIGAND/GAMMA HYDRATED IRON OXIDE SCREENING PROGRAM | | | | |
|---|---|---|---|---|---|
| | FeSO4:Fe in iron oxide | 0 | 0.02 | 0 | 0.02 |
| MILLI-MOLES | Ligand | 19.25 | 19.64 | 19.25 | 19.64 |
| | NH3 | 9.63 | 9.82 | 19.25 | 19.64 |
| | Fe in iron oxide | 17.50 | 17.50 | 17.50 | 17.50 |
| | FeSO4 | 0 | 0.35 | 0 | 0.35 |
| TOTAL GRAMS | | 15.00 | 15.00 | 15.00 | 15.00 |
| pH | initial | 3.17 | 3.20 | 3.36 | 3.37 |
| | final | 3.00 | 2.93 | 1.99 | 1.97 |
| MINUTES TO DISSOLVE | | >150 <180 | >90 <120 | >240 | >240 |

Note:
DTPA reacted @ 100° C. within <180 min, with or without FeSO4, but could not visually distinguish end of reaction.
Iron compounds are expressed in terms of contained Fe
Gamma hydrated iron oxide is Mobay Bayferrox 943

What is claimed is:

1. A process for the preparation of iron organic acid complexes comprising reacting an organic acid or its salt or partial salt that is capable of chelating iron with an oxide of iron and a base in the presence of a trace amount of a separately added a catalyst selected from the group consisting of ferrous ion, metallic iron, and the salt of the ferrous complex of the acid being produced, and neutralizing the resulting reaction product with the further addition of said base.

2. The process of claim 1 wherein said catalyst is ferrous ion.

3. The process of claim 1 wherein said catalyst is metallic iron.

4. The process of claim 1 wherein said catalyst is the salt of the ferrous complex of the acid being produced.

5. The process of claim 1 further comprising oxidizing ferrous ion remaining after said neutralization to ferric ion.

6. The process of claim 1 wherein said acid is an aminocarboxylic acid selected from the group consisting of ethylenediaminetetraacetic acid; nitrilotriacetic acid; iminodiacetic acid; 1,2-propylenediaminetetraacetic acid; N-methyl, ethyl, propyl and butyl iminodiacetic acid; 1,3-propanediaminetetraacetic acid; N-hydroxyethylethylenediaminetriacetic acid; triethylenetriaminehexaacetic acid and diethylenetriaminepentaacetic acid.

7. The process of claim 6 wherein said aminocarboxylic acid is ethylenediaminetetraacetic acid.

8. The process of claim 6 wherein said aminocarboxylic acid is 1,3-propanediaminetetraacetic acid.

9. The process of claim 6 wherein said aminocarboxylic acid is in the form of its salt or partial salt.

10. The process of claim 6 wherein said aminocarboxylic acid comprises a mixture of the free acid and its partial salt.

11. The process of claim 1 wherein said acid is an organic acid selected from the group consisting of citric acid, tartaric acid and gluconic acid.

12. The process of claim 11 wherein said organic acid is citric acid.

13. The process of claim 1 wherein said oxide of iron is selected from the group consisting of magnetite, alpha and gamma hydrated oxides of iron.

14. The process of claim 13 wherein said oxide of iron is synthetic magnetite and the temperature of said mixture is equilibrated to about 40°-60° C.

15. The process of claim 13 wherein said oxide of iron is a natural magnetite and the temperature of said mixture is equilibrated to about 60°-90° C.

16. The process of claim 1 wherein said base is ted from the group consisting of ammonia, sodium hydroxide and potassium hydroxide.

17. The process of claim 16 wherein said base is ammonia.

18. The process of claim 1 wherein the reaction is carried out at a temperature of about 40° C.

19. The process of claim 1 wherein the organic acid is in the form of its salt or partial salt, and is acidified with nitric acid prior to reaction with an oxide of iron.

20. The process of claim 19 wherein said salt is hydroxyethylenediaminetriacetic acid trisodium salt.

21. A process for the preparation of iron organic acid complexes comprising (a) providing an aqueous mixture of an oxide of iron and a base; (b) adding to said mixture an organic acid that is capable of chelating iron; (c) equilibrating the temperature of the mixture to about 40°-80° C.; (d) adding ferrous ion to the mixture to catalyze the reaction; and (e) neutralizing the resulting reaction product with the further addition of said base.

22. The process of claim 21 further comprising oxidizing any remaining ferrous ion to ferric.

23. The process of claim 1 wherein the mole ratio of base:acid is about 0.1–1.5:1.0.

24. The process of claim 21 wherein the mole ratio of base:acid is about 0.1–1.5:1.0.

25. The process of claim 1 further comprising separating the iron complex from any insoluble residue.

26. The process of claim 21 further comprising separating the iron complex from any insoluble residue.

27. The process of claim 25 further comprising crystallizing the separated iron complex.

28. The process of claim 26 further comprising crystallizing the separated iron complex.

29. The process of claim 25 further comprising total drying of the separated iron complex solution.

30. The process of claim 26 further comprising total drying of the separated iron complex solution.

31. The process of claim 29 comprising spray drying the separated iron complex.

32. The process of claim 30 comprising spray drying the separated iron complex.

* * * * *